US008585405B2

(12) United States Patent
Artal Arruga

(10) Patent No.: US 8,585,405 B2
(45) Date of Patent: Nov. 19, 2013

(54) DENTAL IMPLANT WITH AXIAL AND/OR CORONAL MOVEMENT AND METHOD FOR AFFIXING IT

(76) Inventor: Alberto Artal Arruga, Saragossa (ES)

( * ) Notice: Subject to any disclaimer, the term of this patent is extended or adjusted under 35 U.S.C. 154(b) by 37 days.

(21) Appl. No.: 13/146,404

(22) PCT Filed: Feb. 4, 2010

(86) PCT No.: PCT/ES2010/070058
§ 371 (c)(1),
(2), (4) Date: Jul. 27, 2011

(87) PCT Pub. No.: WO2010/089441
PCT Pub. Date: Aug. 12, 2010

(65) Prior Publication Data
US 2011/0287385 A1    Nov. 24, 2011

(30) Foreign Application Priority Data
Feb. 4, 2009  (ES) .................... 200900416

(51) Int. Cl.
*A61C 8/00*        (2006.01)
(52) U.S. Cl.
USPC ........................................... 433/174

(58) Field of Classification Search
USPC ....................... 433/172–176, 201.1
See application file for complete search history.

(56) References Cited

U.S. PATENT DOCUMENTS
5,344,457 A * 9/1994 Pilliar et al. .................... 606/60

* cited by examiner

*Primary Examiner* — Cris Rodriguez
*Assistant Examiner* — Eric Rosen
(74) *Attorney, Agent, or Firm* — Inventa Capital PLC

(57) ABSTRACT

Dental implant that in the event of external pressure is able to absorb a multidirectional pressure, being provided for this purpose with a main body that includes a hollow screw inside which there is a lower end joint, a lower elastic joint, an intermediate nut with internal threading and a hexagonal exterior, an internal movement-limiting screw, an upper elastic joint, a "T"-shaped upper closing part, with a hexagonal head and a threaded interior, where the arrangement and nature of the parts enables not only the dismantling of all of the parts for revision, but also an increase in its strength in response to external forces through its capacity for axial and/or coronal movement, which helps to increase the lifespan of the implant.

12 Claims, 8 Drawing Sheets

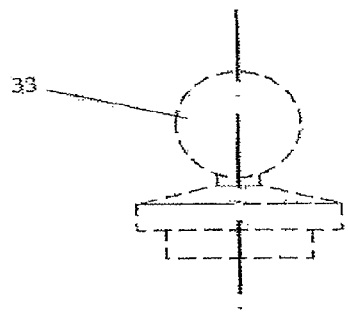
Fig. 1ᵃ -PRIOR ART
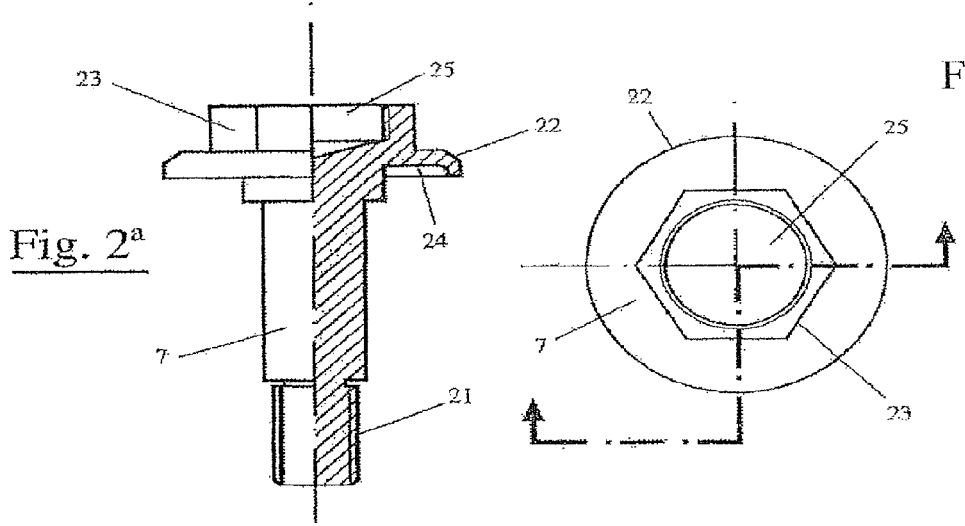
Fig. 2ᵃ   Fig. 2b
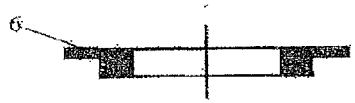
Fig. 3ᵃ

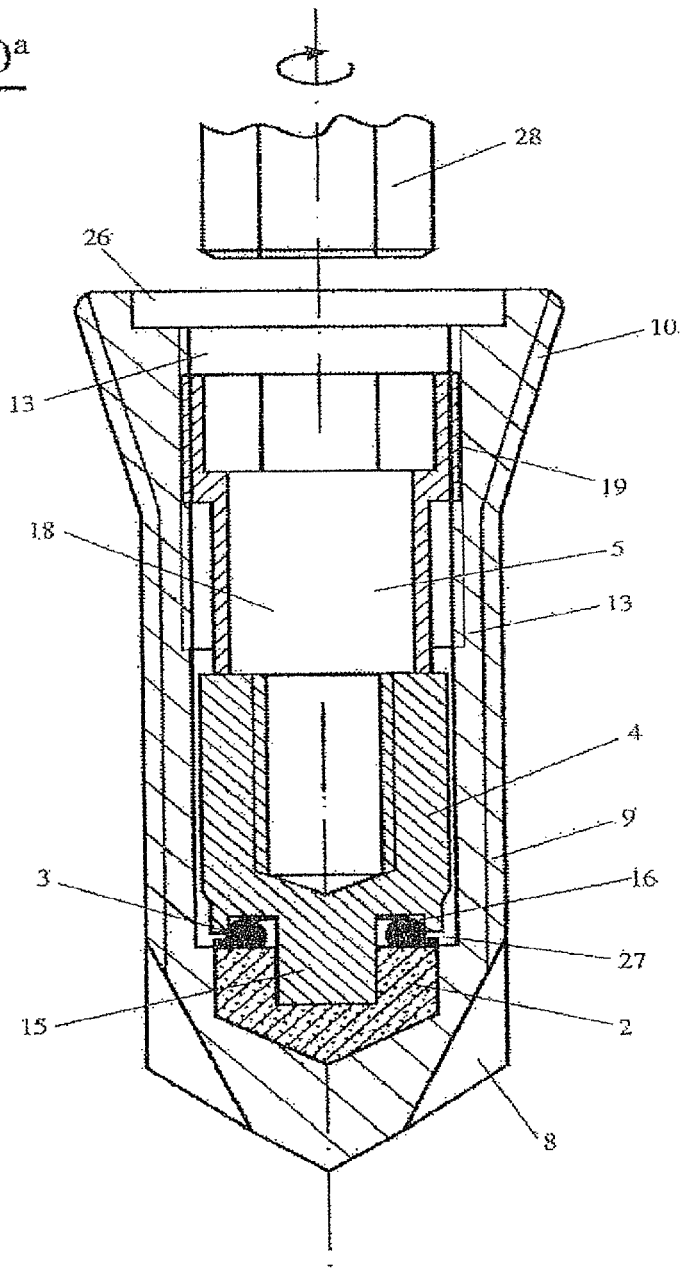

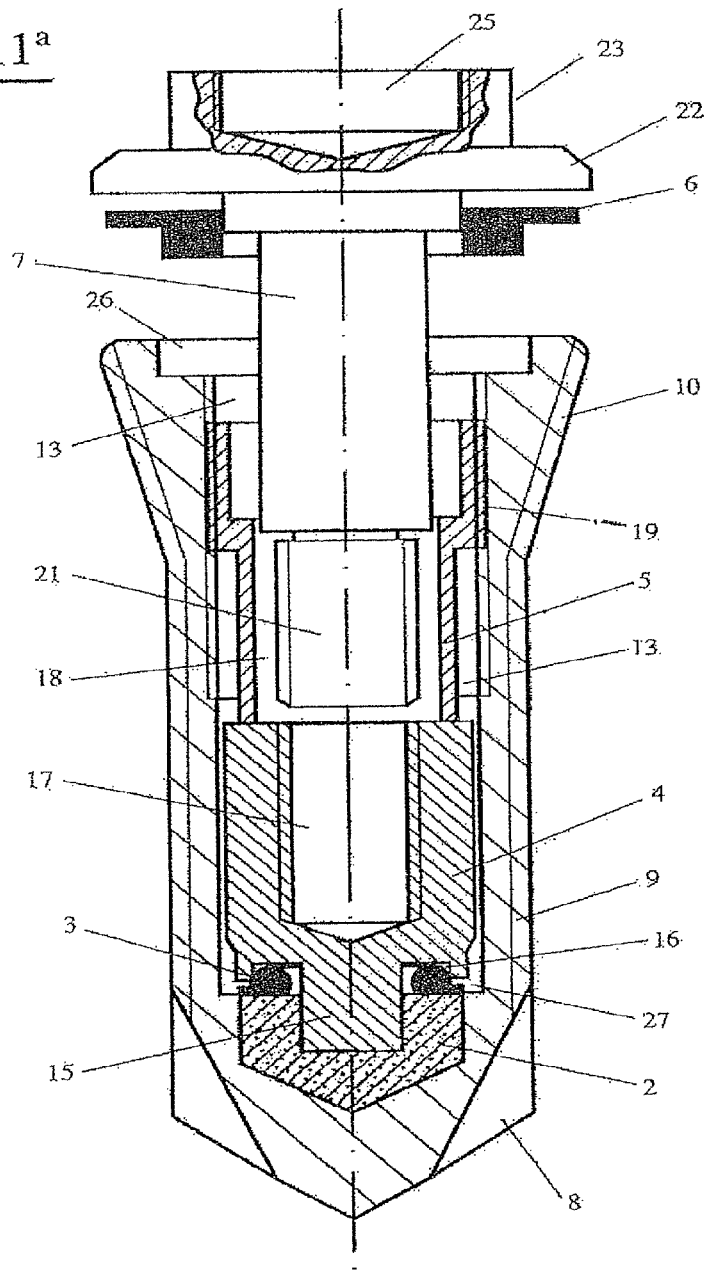

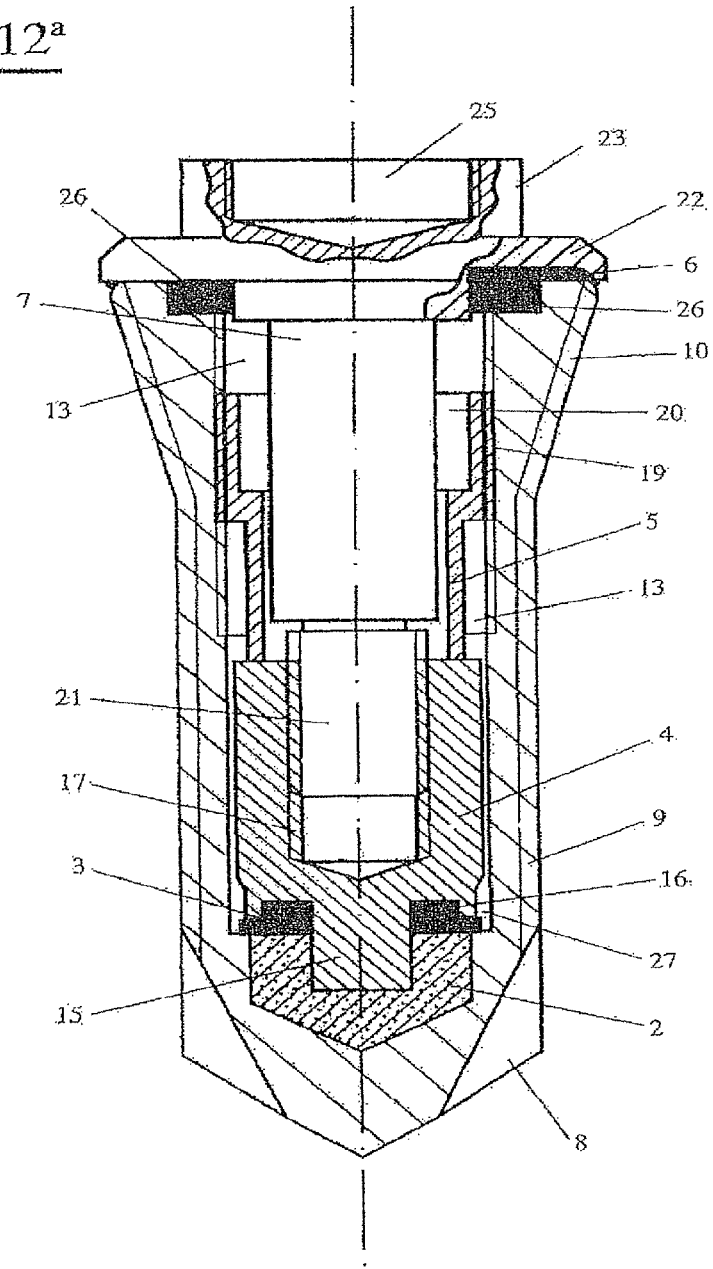

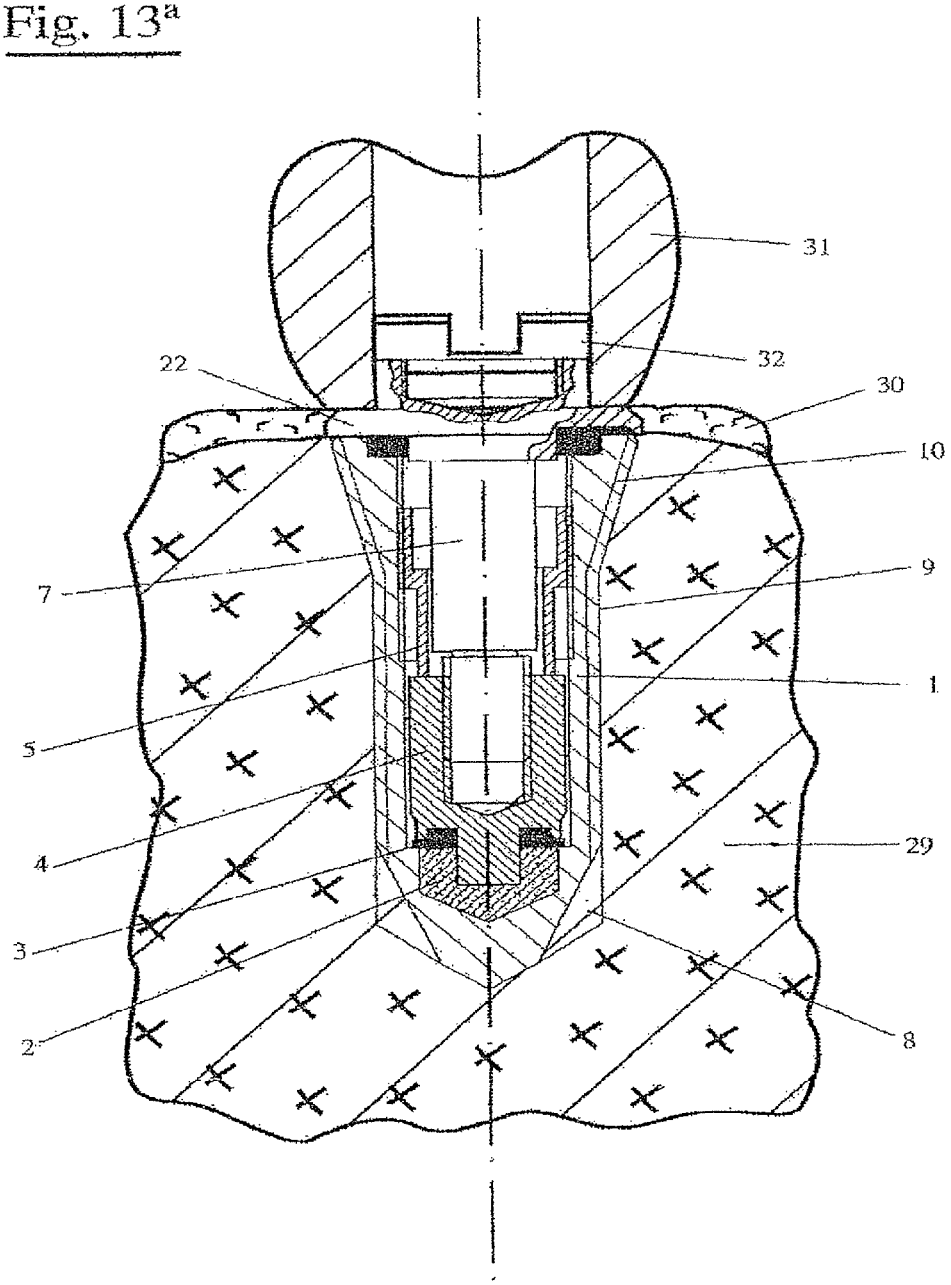
Fig. 13ª

DENTAL IMPLANT WITH AXIAL AND/OR CORONAL MOVEMENT AND METHOD FOR AFFIXING IT

OBJECT OF THE INVENTION

The object of the present invention is a dental implant with axial and/or coronal displacement, and the procedure for assembling the same.

The dental implant of the invention is an osseointegrated implant, i.e., the implant is integrated into the jawbone, acting like a metal socket by way of a hollow screw threaded into the maxilla, so that the various pieces that make up a tooth implant are held and set inside the hollow screw.

This dental implant is characterized by the special configuration and design of each of the pieces that are part of the implant, so that an implant is achieved with the longitudinal axis supported by two pressure absorbers, one located at the bottom of the implant and another at bone crest level, so it achieves a certain axial and/or crown mobility when the tooth is subjected to pressure, to return to its starting position, so that up to a certain pressure it maintains high rigidity, after which it increases flexibility, simulating the behavior of the alveolar dental ligament of natural teeth.

Therefore, the present invention falls within the field of implants, and particularly among those with means to extend the life of the implant.

BACKGROUND OF THE INVENTION

So far osseointegrated dental implants in bone structure are a series of pieces fixed in a solid screw that is screwed into the maxilla.

One of the difficulties with this type of implant is the pressure they are under, which could lead to deterioration of the tooth and the very structure of the implant.

The pressures to which implants are subjected are derived from the pressure of work, such as chewing. Normal chewing exerts a pressure of 100 kg/mm2 and can reach 160 kg/mm2 in patients suffering from bruxism.

These situations cause the reduction of life of the implant. Therefore, it is an objective of this invention to develop a dental implant which, although it may be subjected to such pressures, may have elements capable of absorbing the pressure on the implants, which necessarily have an impact on the life of the implant.

On the other hand, it is intended that the implant can be removed, a fact which is very useful when you make changes to the prosthesis or when making a new prosthesis.

DESCRIPTION OF THE INVENTION

The present invention of a dental implant with axial and/or coronal displacement, as the name suggests, is a dental implant which, when subjected to external pressure, is able to absorb this pressure, being provided for this with structure and means to accommodate pressure absorbers, without this involving significant displacement of the implant.

This implant consists of a main body consisting of a hollow screw inside which the other pieces are arranged.

All references to "lower" or "upper" are made with reference to the final position of the implant.

The main body, consisting of a hollow screw, has two threaded outer zones, one arranged on the bottom that is cylindrical and the other, an exterior threaded portion, on the top, which has the shape of an inverted truncated cone. Inside this piece there are three areas, a lower housing for a buffer, an intermediate hexagonal cross section, and a threaded upper part.

Inside the hollow screw the following parts are arranged, as presented below. They are set out to follow their arrangement inside the screw, from the bottom to the top of the implant.

Lower end joint, made in elastic material.

Bottom gasket, also made in elastic material.

Intermediate nut with inside thread, having at its lower part an end with a lug and hexagonal walls.

Internal screw with movement limiter

Upper elastic joint

Top closing piece, which has a "T" shape, which has its threaded inner end, a central part, and an upper part shaped like a hex head which is threaded inside to house the crowns.

The assembly procedure of this implant with axial and/or coronal displacement comprises the following steps:

Fixing the threaded socket to the maxilla by means of its two external surface areas.

Insertion of the lower fixation joint

Positioning of the lower elastic joint.

Fixing of the interior threaded nut.

Introduction of the internal screw limiting the movement of the internally threaded nut, positioned inside and immediately below the internal screw.

Introduction of the closing body, which will already be fitted with the upper elastic seal Screwing of the lower part of the closing body into the inside thread of the internal nut.

Once the implant is loaded and with the joints in their rest position, there will be no movement in any direction. But a working situation, that is, during chewing, where the working pressure can reach 100 kg/mm2, and even 160 kg/mm2 for patients with bruxism, will cause the expansion of the upper and lower elastic joints, filling expansion slots provided for this purpose, returning to the original position when the person stops exerting such pressure.

With this setup, once the implant is osseointegrated, it is possible to review and remove each of the interior parts separately. This disassembly process will not be necessary during the early years, but it will be very useful when changes need to be made in the prosthesis or when it has to be replaced by a new prosthesis.

As a result of the provision of means of absorbing the axial and/or coronal pressure exerted by chewing, the other elements of the implant will be subjected to lower pressure, resulting in less stress and therefore a longer life for the implant.

EXPLANATION OF FIGURES

To complement the description that will be made and in order to help better understand their characteristics, this specification is accompanied by a set of drawings in whose figures, by way of illustration and not limitation, the most significant details of the invention are represented.

FIG. 1a shows a spherical type of fixation (33) of the crowns or dentures, to suit existing implants, and this may take other forms from those already on the market, such as conical etc. . . . . .

FIG. 2a shows a 90° longitudinally sectioned elevation; FIG. 2b shows a top view of the sealing body (7).

FIG. 3a shows a cross section of the elastic circular seal (6).

FIG. 10*a* shows a longitudinal section view of the placement of the implant prior to placement in the maxilla, in which we see how the pieces (2-3-4 and 5) are positioned axially inside the main body (1). The piece (5) is screwed on (19) inside the body (1), and held in place by its end piece (4) for stabilization.

FIG. 11*a* shows a longitudinal section view of an implant placement, prior to placement in the maxilla, in which we see how the pieces (2-3-5 4-5-6 and 7) are positioned axially inside the main body (1). The piece (6) as a joint is placed in the upper body (7), and in turn these are screwed into the threaded portion (21) of the inside thread (17) of piece (4) that is stabilized inside the body (1) so that the nut cannot move, held in place by part (5). We also see the expansion area (27) of the joint (3).

FIG. 12*a* shows a finished placement ready to be placed in the maxilla. We see the assembly that is made once the pieces are placed in the maxilla, where we may now place the corresponding crowns and dentures (31).

FIG. 13*a* shows the assembly mounted in the bone of a maxilla (29).

PREFERRED USE OF THE INVENTION

Figure 4A:
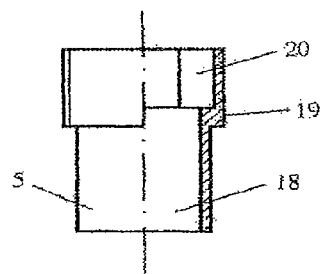
FIG. 4a shows a 90° longitudinally sectioned elevation.

By means of the figures, we describe below a preferred method of using the proposed invention.

FIG. 13*a* shows the entire osseointegrated implant assembly, which shows all 30 pieces of the same and how they are coupled together.

FIG. 1*a* shows a simplified spherical fixation (33) that is already on the market for securing crowns or dentures (31), this being the end fixing of the body (1).

The pieces that make up the implant are:
The main body or hollow screw, shown in FIGS. 8*a*-8*c*.
The top joint as shown below in FIGS. 7*a*-7*b*.
Bottom gasket, shown in FIGS. 6*a*-6*b*.
Interior intermediate threaded nut, shown in FIGS. 5*a*-5*b*.
Internal screw limiting the movement shown in FIGS. 4*a*-4*b*.
Upper elastic joint, shown in FIG. 3*a*.
Top closing piece, shown in FIGS. 2*a*-2*b*.

We proceed to describe each of the pieces that make up the implant, their characteristics of construction and how they are coupled with the other pieces. So in FIGS. 8*a*-8*c*, which show the main body or hollow screw (1), we see that there is a generally cylindrical configuration, modified at its ends so that the lower end has a pointed shape that has a series of cuts or slots (8) to facilitate insertion into the bone. In the central part there is a cylindrical exterior threaded area (9), wide cut with a fine thread and sufficient distance of movement for smooth integration into the bone. The top of the hollow screw (1) generally having a configuration in the form of a truncated inverted cone on the outside has a threaded portion (10) which is cut thinner, with less cutting and a smaller thread.

In the interior of the hollow screw (1) three areas can be distinguished, a lower zone (11) with an end joint (2), above which there is a intermediate zone (12) with hexagonal walls that serve to lock the intermediate nut (4), which allows the intermediate nut (4) an axial displacement only, i.e. along the vertical axis of the hollow screw (1). Finally, in the upper part of the inside of the hollow screw (1) there is an upper area (13) of a threaded wall where an internal screw thread (5) limits the movement of the nut (4).

Figure 7A:
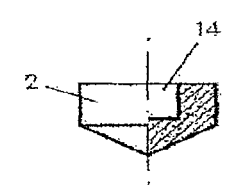
FIG. 7*a* shows a 90° longitudinally sectioned elevation.
Figure 7B:
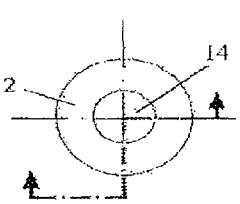
FIG. 7*b* shows a top view of the frontal fixation joint of the elastic material (2), which will absorb the axial and/or coronal pressure.
Figure 8B:
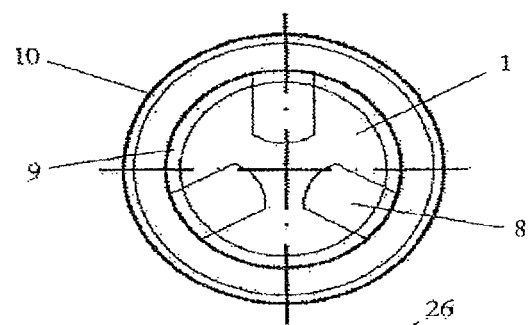
FIG. 8*b* shows a top view and FIG. 8*c* shows a bottom plan view of the screw (1).
Figure 8A:
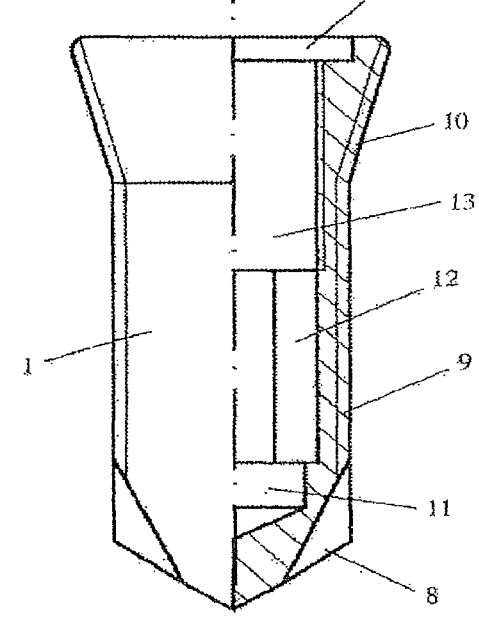
FIG. 8*a* shows a 90° longitudinally sectioned elevation.
Figure 8C:
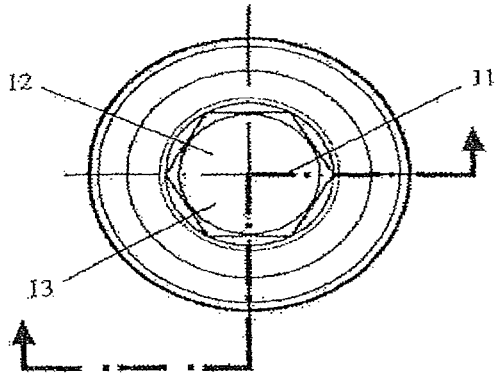

FIGS. 7*a*-7*b* show the section and plan of the fixation joint (2), which has a generally cylindrical configuration which is tapered at the bottom, presenting a cylindrical housing (14) which holds the lug (15) (FIGS. 5*a*-5*b*) presented at the lower end of the nut (4) with the interior thread (17).

Figure 5A:
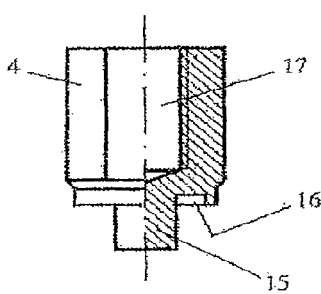
FIG. 5*a* shows a 90° longitudinally sectioned elevation.
Figure 5B:
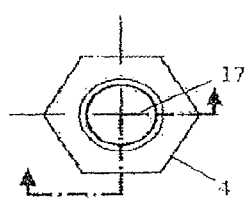
FIG. 5*b* shows a top view of the inner nut (4).

FIGS. 5*a*-5*b* show the section and plan of the nut (4), which as we have said has a lug (15) at its bottom, presenting an interior threaded area, while its outer walls have a hexagonal shape, fitting into the intermediate area (12) of the hollow screw (1).

Figure 6A:
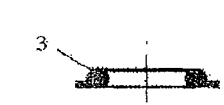
FIG. 6*a* shows a cross section of the elastic intermediate elastic joint (3)
Figure 6B:
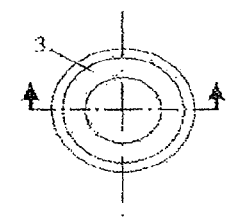
FIG. 6*b* shows a top view of the elastic intermediate elastic joint (3).

The lower lug (15) is of a smaller section than the rest of the body, so that in the escalation between the two parts a recess (16) is defined for housing the lower elastic joint (3) shown in (FIGS. 6*a*-6*b*).

Figure 4B:
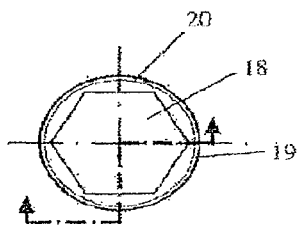
FIG. 4b shows a top view of the screw (5).

FIGS. 4*a*-4*b* show the internal screw (5) limiting the movement of the nut (4). This internal screw (5) has a generally hollow cylindrical configuration which is distinguished by a smooth cylindrical bottom part (18) whose lower part makes contact with the top of the nut (4) and through the surface contact of both these parts the pressure is transmitted from the screw (5) to the nut (4).

After the smooth cylindrical bottom (18), there is a threaded cylindrical upper part (19) on the outside. The exterior of the upper thread (19) of the screw (5) screws into the internal threads of the threaded area (13) of the hollow screw (1). Thus, by screwing the screw (5) against the hollow screw (1) it is possible to transmit pressure to the nut (4), achieving the axial movement of this piece, and limiting its subsequent movement to the extent appropriate for the assembly.

Finally, this screw (5) presents a hollow hexagonal head (20) on which a key (28) shown in (FIG. 10*a*) places an adjustment pressure on the screw (5). This key (28) is a fixing tool which is not part of the implant.

Finally the closing piece (7) is fixed as shown in FIGS. 2*a*-2*b*. This piece has an overall configuration in a "T", and is generally cylindrical in section, presenting at its lower end a threaded portion (21) that screws into the inside threads (17) of the nut (4).

After the threaded portion (21) there is a shank, where both pass through the screw (5) limiting movement of the nut (4). In the top of the closing piece (7) lies the closing head (22), with a width greater than the rest of the barrel, and the bottom surface of said head end (22) defines an annular recess (24) to accommodate the upper seal (6) shown in (FIG. 3*a*). On the head end (22) of the closing piece (7) there is an area which has a hexagonal outer surface (23) for closing and tightening the locking piece (7), while centered on that ledge there is a central well with an internal thread (25) where the crowns are screwed in.

The upper gasket (6) (FIG. 3*a*) is not only accommodated in the recess (24) in the lower side of the head (22) of the closing piece (7) but also in the annular recess (26) that is on the top of the hollow screw (1).

Figure 9A:
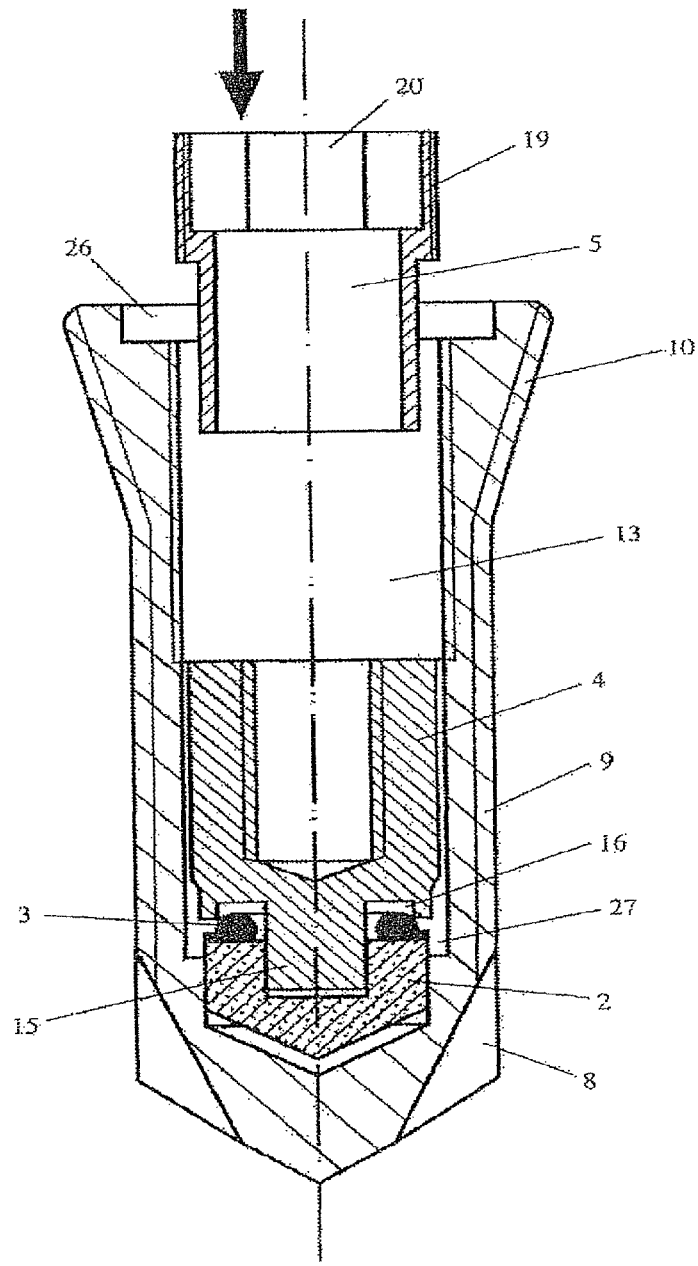
FIG. 9*a* shows a longitudinal section view of the beginning of the implant placement, prior to placement in the maxilla, in which we see how the pieces (2-3 and 4) are positioned axially inside the main body (1). The piece (4) cannot rotate inside the body (1) since the two parts have complementary hexagonal walls.

The elastic joints (3) and (6) have their own areas of expansion. So in FIG. 9a we can see that the lower elastic joint (3) has an expansion zone (27) that allows the absorption of axial and/or coronal elastic impacts. Thus in FIG. 12a, the expansion can be seen of both the lower (3) and upper (6) joints, which have partially filled the areas allocated for expansion.

Finally, FIG. 13a shows how the implant is housed in relation to the maxilla (29) and the area of the gum or mucosa (30), it being possible to see the crown (31) or prosthesis that the patient requires, which is visible from the outside. It also shows the screw (32) fixing the crown (31) to the rest of the implant.

The essence of this invention is not changed by variations in the materials, shape, size and arrangement of the component elements, described in non-limiting terms which are sufficient for its reproduction by an expert.

The invention claimed is:

1. Dental implant with axial and/or coronal displacement comprising:
  a) a main body in the form of a hollow screw (1) which
    i. externally comprises a cylindrical configuration, comprising:
      A. a lower end with a pointed form,
      B. a middle portion comprising a cylindrical exterior threaded area (9), and
      C. an upper portion comprising a configuration as an inverted truncated cone; wherein the inverted truncated cone comprises an outer threaded portion (10),
    ii. internally: the hollow screw comprises:
      A. a lower zone (11) where an end joint (2) is housed,
      B. an intermediate zone (12) above the lower zone; wherein the intermediate zone comprises hexagonal walls that serve to lock a nut (4), and
      C. an upper threaded wall (13) above the intermediate zone;
  wherein inside of the hollow screw (1), the following pieces are arranged from the bottom of the implant to the top;
    i. the end joint (2) housed in the lower zone (11) of the hollow screw (1),
    ii. a lower elastic joint (3),
    iii. the nut (4); wherein the nut comprises a threaded interior (17) and a hexagonal outside,
    iv. an internal screw (5) limiting the movement of the nut (4); wherein the internal screw comprises a smooth cylindrical bottom (18) and an upper cylindrical threaded part (19) above the smooth cylindrical bottom (18),
    v. an upper elastic joint (6), and
    vi. an upper closing part (7).

2. Dental implant with axial and/or coronal displacement according to claim 1, wherein the hollow screw (1), at the lower end with the pointed form, is provided with a series of cuts or slots (8); wherein the cylindrical exterior threaded area (9) is wide cut with a fine thread and long barrel and wherein the outer threaded portion (10) is finer cut, shorter and with smaller thread compared to the cylindrical exterior threaded area.

3. Dental implant with axial and/or coronal displacement according to claim 1, wherein the end joint (2) has a cylindrical configuration which comprises a bottom which is tapered and wherein the end joint comprises a cylindrical inner housing (14).

4. Dental implant with axial and/or coronal displacement according to claim 1, wherein the nut (4) comprises an underside with a lug (15), wherein the hexagonal outside of the nut fits into the intermediate zone (12) of the hollow screw (1).

5. Dental implant with axial and/or coronal displacement according to claim 4, wherein the lug (15) has a smaller diameter than a body of the nut, so that a recess (16) is defined between the lug and the body of the nut for housing the lower elastic joint (3).

6. Dental implant with axial and/or coronal displacement according to claim 5 wherein the lower elastic joint (3) expands within the recess (16).

7. Dental implant with axial and/or coronal displacement according to claim 1, wherein the smooth cylindrical bottom (18) makes contact with a top of the nut (4), wherein through the contact, pressure is transmitted from the internal screw (5) to the nut (4); wherein the upper cylindrical threaded part (19) screws into an inside thread of the upper threaded wall (13) of the hollow screw (1).

8. Dental implant with axial and/or coronal displacement according to claim 7, wherein the internal screw (5), comprises a head with a hexagonal inner cavity (20) on which a key (28) can act.

9. Dental implant with axial and/or coronal displacement according to claim 1, wherein the upper closing part (7) has a T-shaped configuration; wherein the upper closing part (7) comprises a cylindrical section, the cylindrical section comprising a threaded portion (21) at a lower end; wherein the threaded portion (21) screws into the threaded interior (17) of the nut (4), wherein the closing part further comprises a shank above the threaded portion (21), wherein both the threaded portion (21) and the shank pass through the internal screw (5) limiting the movement of the nut (4), wherein a top of the closing part (7) has a closing head (22) having a width greater than the threaded portion (21) and the shank, wherein a bottom surface of said closing head (22) defines a recess ring (24) for accommodating the upper elastic joint (6).

10. Dental implant with axial and/or coronal displacement according to claim 9, wherein, on the closing head (22) of the upper closing part (7) there emerges a central projection comprising a hexagonal outer surface (23) for closing and tightening the closing piece part (7), wherein the central projection further comprises a hollow interior thread (25) where crowns are configured to be threaded accordingly.

11. Dental implant with axial and/or coronal displacement according to claim 9, wherein the upper elastic joint (6) remains in the recess ring (24) on the underside of the closing head (22) of the closing part (7) and also in an annular recess (26) that is on the top of the hollow screw (1).

12. Dental implant with axial and/or coronal displacement according to claim 9 wherein the upper elastic joint (6) expands outside of the hollow screw.

* * * * *

UNITED STATES PATENT AND TRADEMARK OFFICE
CERTIFICATE OF CORRECTION

| | | |
|---|---|---|
| PATENT NO. | : 8,585,405 B2 | Page 1 of 1 |
| APPLICATION NO. | : 13/146404 | |
| DATED | : November 19, 2013 | |
| INVENTOR(S) | : Alberto Artal Arruga | |

It is certified that error appears in the above-identified patent and that said Letters Patent is hereby corrected as shown below:

In the Claims:

Column 6:

Claim 10, line 47 should be corrected as follows:

Change:

--tightening the closing piece part (7), wherein the central--
to
"tightening the closing part (7), wherein the central"

Signed and Sealed this
Eleventh Day of February, 2014

Michelle K. Lee
*Deputy Director of the United States Patent and Trademark Office*